(12) United States Patent
Staples et al.

(10) Patent No.: US 6,354,160 B1
(45) Date of Patent: *Mar. 12, 2002

(54) METHOD AND APPARATUS FOR IDENTIFYING AND ANALYZING VAPOR ELEMENTS

(75) Inventors: Edward J. Staples, Thousand Oaks; Gary Watson, Newbury Park, both of CA (US)

(73) Assignee: Electronic Sensor Technology, LLP, Newbury Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/303,022

(22) Filed: Apr. 30, 1999

Related U.S. Application Data

(63) Continuation of application No. 08/820,671, filed on Mar. 18, 1997, now Pat. No. 5,970,803.
(60) Provisional application No. 60/013,891, filed on Mar. 22, 1996.

(30) Foreign Application Priority Data

Mar. 25, 1996 (JP) .......................... 0996-67973

(51) Int. Cl.⁷ ............................................... G01N 25/18
(52) U.S. Cl. ................................................. 73/863.12
(58) Field of Search .................... 73/863.12, 863.21, 73/863.23, 863.24, 863.72, 863.73, 864.72, 864.81, 864.83, 23.41, 23.42

(56) References Cited

U.S. PATENT DOCUMENTS 3,768,300 A * 10/1973 Nemeth
5,162,652 A * 11/1992 Cohen et al.
5,289,715 A * 3/1994 Staples et al.
5,970,803 A * 10/1999 Staples et al.

\* cited by examiner

Primary Examiner—Robert Raevis
(74) Attorney, Agent, or Firm—Gene W. Arant; William S. Lovell

(57) ABSTRACT

A method and apparatus for identifying and analyzing vapor elements, using a preconcentrator collector. The preconcentrator collector collects and preconcentrates chemical vapors to be detected and identified before chromatographic analysis using surface acoustic wave gas chromatograph (SAW/GC) technology. The preconcentrator collector is used in conjunction with a sensor in an SAW/GC detector in the apparatus. A physical parameter associated with the sensor changes in a defined manner upon exposure of the sensor to an unknown vapor, permitting identification of the individual vapor elements. The preconcentrator collector of the invention includes a body portion having an inlet and an outlet, and a stack of collector plates disposed in the body portion. The collector plates are made of a material that is easily micromachinable and easily cleanable, such as silicon, silica or fused quartz. The outlet of the body portion is connectable to a sampling pump for taking a sample of ambient air into the body portion through the inlet. After the sample is taken, the collector plates trap the chemical vapors in the sample of ambient air and non-trapped vapors exit through the outlet. By using the preconcentrator collector, the present invention achieves more specificity and selectivity simultaneously with high sensitivity.

20 Claims, 8 Drawing Sheets

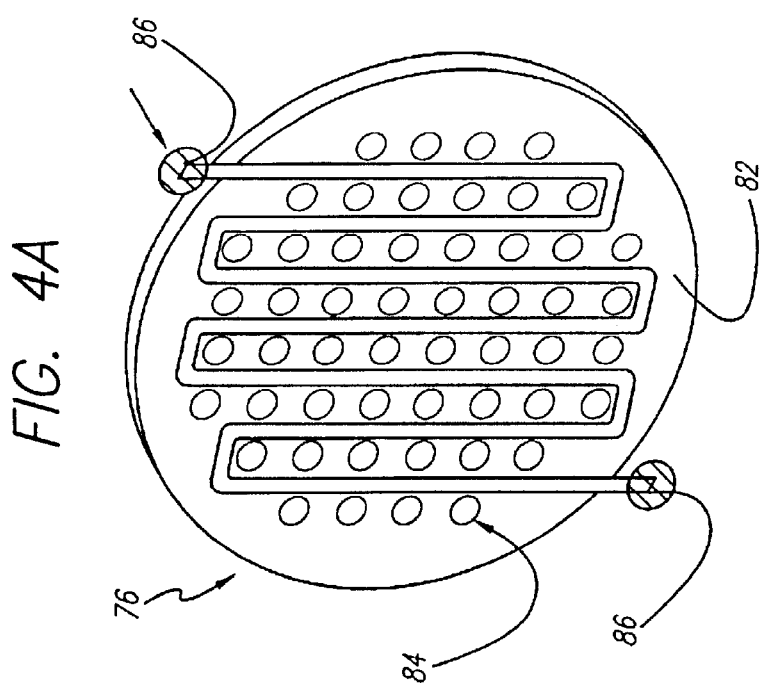
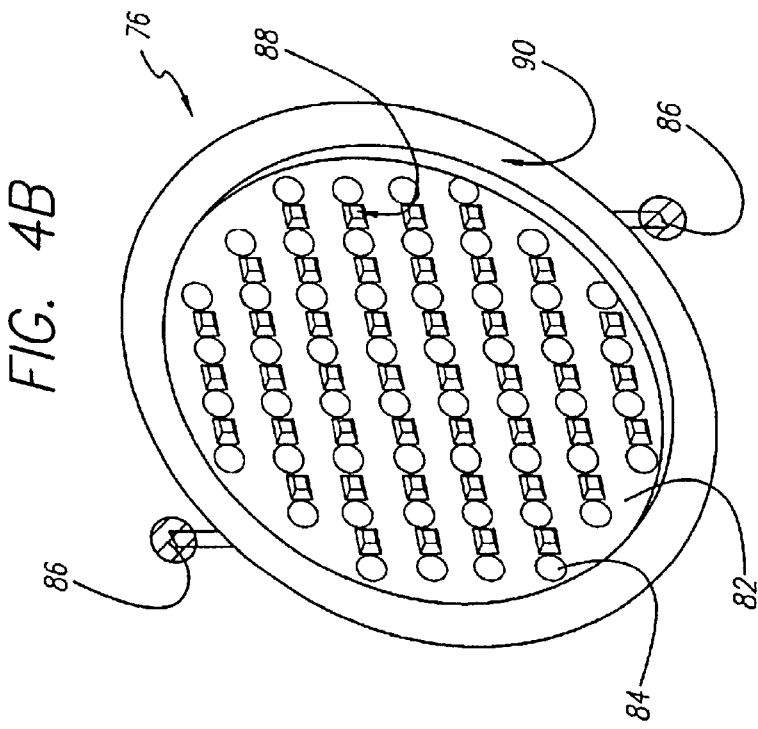

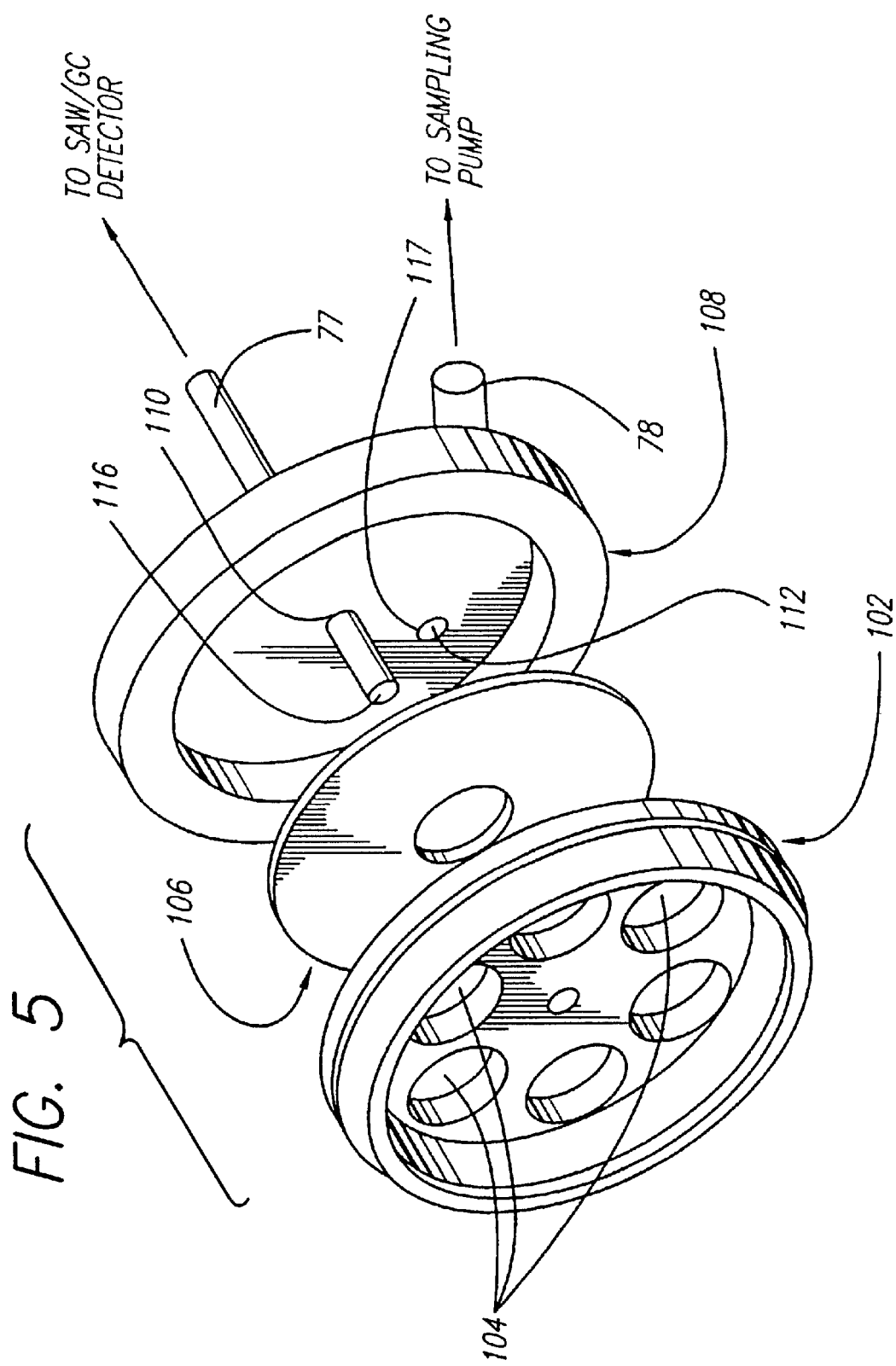

METHOD AND APPARATUS FOR IDENTIFYING AND ANALYZING VAPOR ELEMENTS

CROSS-REFERENCE TO RELATED APPLICATIONS

This application is a continuation of and incorporates by reference patent application entitled "Method and Apparatus For Identifying And Analyzing Vapor Elements" Ser. No. 08/820,671, filed on Mar. 18, 1997, (and now U.S. Pat. No. 5,970,803), by inventors Edward J. Staples and Gary Watson.

A claim for priority is hereby made to a U.S. Provisional Application Ser. No. 60/013,891, filed on Mar. 22, 1996.

BACKGROUND OF THE INVENTION

1. Field of the Invention

The invention relates to a method and apparatus for identifying and analyzing vapor elements, and more particularly to a surface acoustic wave gas chromatographic (SAW/GC) with a preconcentrator collector and a method of using same.

2. Related Art

In the analysis of chemical vapors there is frequently a need to detect extremely small trace amounts of a specific vapor amongst a background of different chemical species. Examples are the detection of contraband aboard the cargo of vessels being inspected by the United States Coast Guard and the detection of leaking explosive or dangerous chemicals at depositories thereof. Automated or portable testing apparatus for this purpose has generally not been available. Further, existing detectors are only able to detect chemical species at concentrations well above their ambient vapor concentrations and thus lack sufficient sensitivity.

Chemical sensors have been developed that physically change upon exposure and contain absorbing polymers selected for their affinity to absorb a group of related chemical species. One type, surface acoustic wave (SAW) delay line sensors, are the most developed and readily available. For example, one commercial supplier is Microsensor System, Inc., Fairfax, Va.

A method and apparatus for using an SAW device to detect a vapor is disclosed by H. Wohltjen in U.S. Pat. No. 4,312,228, issued Jan. 26, 1982. As described therein, the SAW device comprises a piezoelectric element having a surface coated with a polymer material selected to absorb and react with the chemical to be detected. Interaction of the chemical with the material coating of the sensing element alters one or more properties of a surface acoustic wave, and the electrodes on the piezoelectric element detect the altered wave, producing an electrical signal.

Another apparatus and method for detection and identification of chemical vapors is disclosed in U.S. Pat. No. 4,895,017. As described in a plurality of surface acoustic wave (SAW) devices, each coated with a selected polymer material, are exposed to the vapor to be analyzed. In this invention a predicted time constant (or rate) of diffusion into the polymer coating is used to identify the different chemical species. To quantitatively identify specific chemical species present in vapors an array of SAW sensors with different polymer coatings may be exposed and a pattern recognition technique utilized to identify specific species. This is described in a paper entitled "Correlation of Surface Acoustic Wave Device Coating Responses With Solubility Properties and Chemical Structure" by D. S. Ballentine, Jr., S. L. Rose, J. W. Grate, and H. Wohltjen, published in Analytical Chemistry, Vol. 58, p. 3058, December 1986.

A further patent using multiple polymer coated dispersive delay lines is disclosed by J. Haworth in U.S. Pat. No. 5,012,668, issued May 7, 1991. The use of specific absorbant polymers to sensitize the surface of a piezoelectric crystal and induce a phase or amplitude variation in a traveling acoustic wave is common to all of the prior art and this approach severely limits the performance of these vapor detectors. Multiple polymer films dilute the vapor samples and thereby limit the amount of vapor that can be detected by each film. Also, practically any type of film applied to the surface of a piezoelectric crystal introduces noise which reduces sensitivity further.

In view of such problems, the present inventors have proposed an apparatus for performing high speed detection and identification of vapor species. The apparatus includes a temperature programmed vapor preconcentrator for trapping condensable vapor species, a multi-port valve, a temperature programmed chromatographic capillary column, an acoustic wave interferometer for detecting adsorption and desorption of vapor species, a thermoelectric heating and cooling element for controlling the temperature of the acoustic interferometer sensor, and an electronic system controller which is described by the present inventors, i.e., Staples et al., in U.S. Pat. No. 5,289,715, which is hereby incorporated by reference. This apparatus is capable of detecting trace elements with high specificity and sensitivity. The detection can be done near real time.

SUMMARY OF THE INVENTION

It is an object of the present invention to achieve more specificity and selectivity simultaneously with high sensitivity by providing a preconcentrator collector for preconcentrating chemical vapors to be detected and identified before chromatographic analysis.

It is another object of the present invention to provide improved performance over the conventional surface acoustic wave gas chromatography (SAW/GC) technology.

According to a first aspect of the present invention, a preconcentrator collector is provided for collecting and preconcentrating chemical vapors from a sample of ambient air. The preconcentrator collector comprises a body having an inlet and an outlet that is connectable to a sampling pump for taking the sample of ambient air into the body through the inlet. The preconcentrator collector also includes a stack of collector plates made of a material that is easily micromachinable and easily cleanable, such as silicon, silica or fused quartz, and disposed in the body. According to the invention, after the sample is taken, the collector plates trap the chemical vapors in the sample of ambient air and non-trapped vapors exit through the outlet.

According to a second aspect of the present invention, there is provided an apparatus for identifying and analyzing chemical vapors from a sample of ambient air. The apparatus comprises a sampling pump, a preconcentrator collector coupled to the sampling pump for collecting and preconcentrating chemical vapors taken from the sample of ambient air; a separating means for separating individual vapor species in the chemical vapors desorbed from the collector plates of the preconcentrator collector according to their speeds in traveling through the separating means; and a detecting means for detecting and identifying the individual vapor species output from the separating means. The separating means may be made of a metal capillary column heatable by applying an electric current thereto.

According to a third aspect of the present invention, there is provided a method of detecting and identifying chemical vapors from a sample of ambient air. The method comprises the steps of collecting and preconcentrating chemical vapors taken from the sample of ambient air using a preconcentrator collector; separating, using a separating means, individual vapor species in the chemical vapors desorbed from the collector plates of the preconcentrator collector according to their speeds in traveling through the separating means; and detecting and identifying the individual vapor species output from the separating means using a surface acoustic wave gas chromatographic (SAW/GC) detector.

BRIEF DESCRIPTION OF THE DRAWINGS

FIGS. 4A and 4B show the front and back sides of a micromachined silicon collector plate used in the preconcentrator collector of the present invention;

FIG. 5 shows an exploded view of a sampling valve used in the preconcentrator collector of the present invention;

DETAILED DESCRIPTION OF THE PREFERRED EMBODIMENTS

Figure 1:
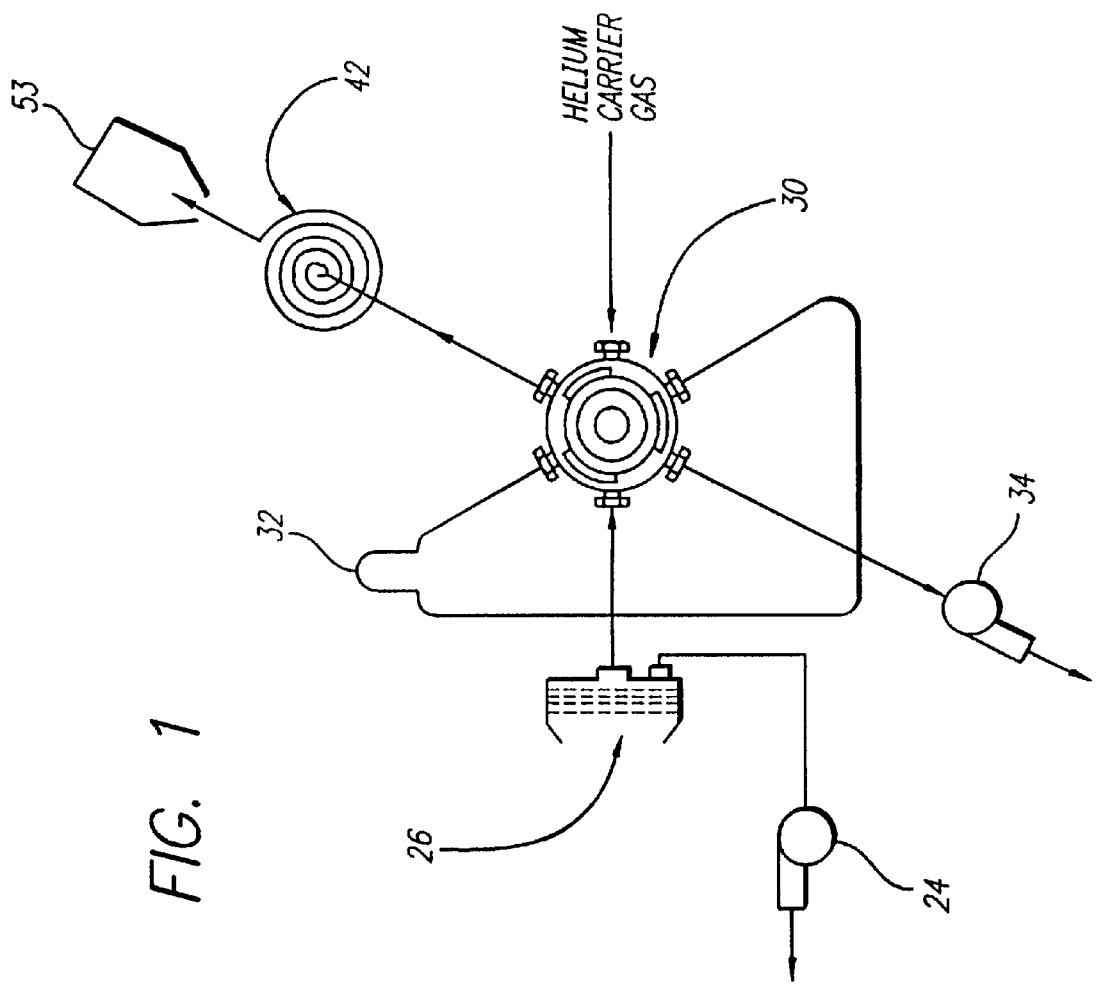
FIG. 1 shows an SAW/GC system according to an embodiment of the present invention.

FIG. 1 shows an SAW/GC (surface acoustic wave gas chromatographic) system according to the invention. The SAW/GC system comprises a sampling pump 24, a preconcentrator collector 26, a six-port GC valve 30, a loop trap section 32, a vacuum pump 34, a capillary GO column 42 and a SAW detector 53.

In order to achieve specificity and selectivity simultaneously with high sensitivity, a silicon collector preconcentrator 26 is utilized in a preferred embodiment of the SAW/GC detection system according to the invention. In gas chromatography, a sample containing many different chemical species is taken by collector preconcentrator 26 through the use of a sampling pump 24. The sample then passes through GC valve 30 and enters into capillary column 42 together with an inert carrier gas such as helium. As the chemicals travel along the capillary they interact with the chemical coating of capillary column 42 and are slowed by the interaction. Since each interaction is chemically different, the individual chemical species exit capillary column 42 dispersed in time. By measuring the time to transit capillary column 42, the individual species can be identified. By using a nozzle, the effluent from capillary column 42 is focused into an area of SAW resonator containing the highest intensity of standing acoustic waves in SAW detector 53, whereby the chemical species will be detected only if they are adsorbed onto a crystal surface of a sensor in SAW detector 53. An example of SAW detector and its operation is disclosed in U.S. Pat. No. 5,289,715, which has been incorporated by reference.

By means of a six-port GC valve, ambient air is sampled, aerosols trapped, and then injected into the helium flow to capillary column 42. In FIG. 1, The SAW/GC system will sample vapor from the ambient environment through a silicon or silica preconcentrator collector 26 and sampling pump 24. Preconcentrator collector 26 serves the dual purpose of selectively adsorbing vapors or particles from the air and allowing large volumes of air to be sampled while minimizing the volume of the preconcentrator collector itself. After the vapors or particles are adsorbed, the output of preconcentrator collector 26 is cycled via a sampling valve in the preconcentrator collector to allow the vapor generated from the thermal desorption at preconcentrator collector 26 to enter loop trap section 32 and stick thereon.

Figure 2:
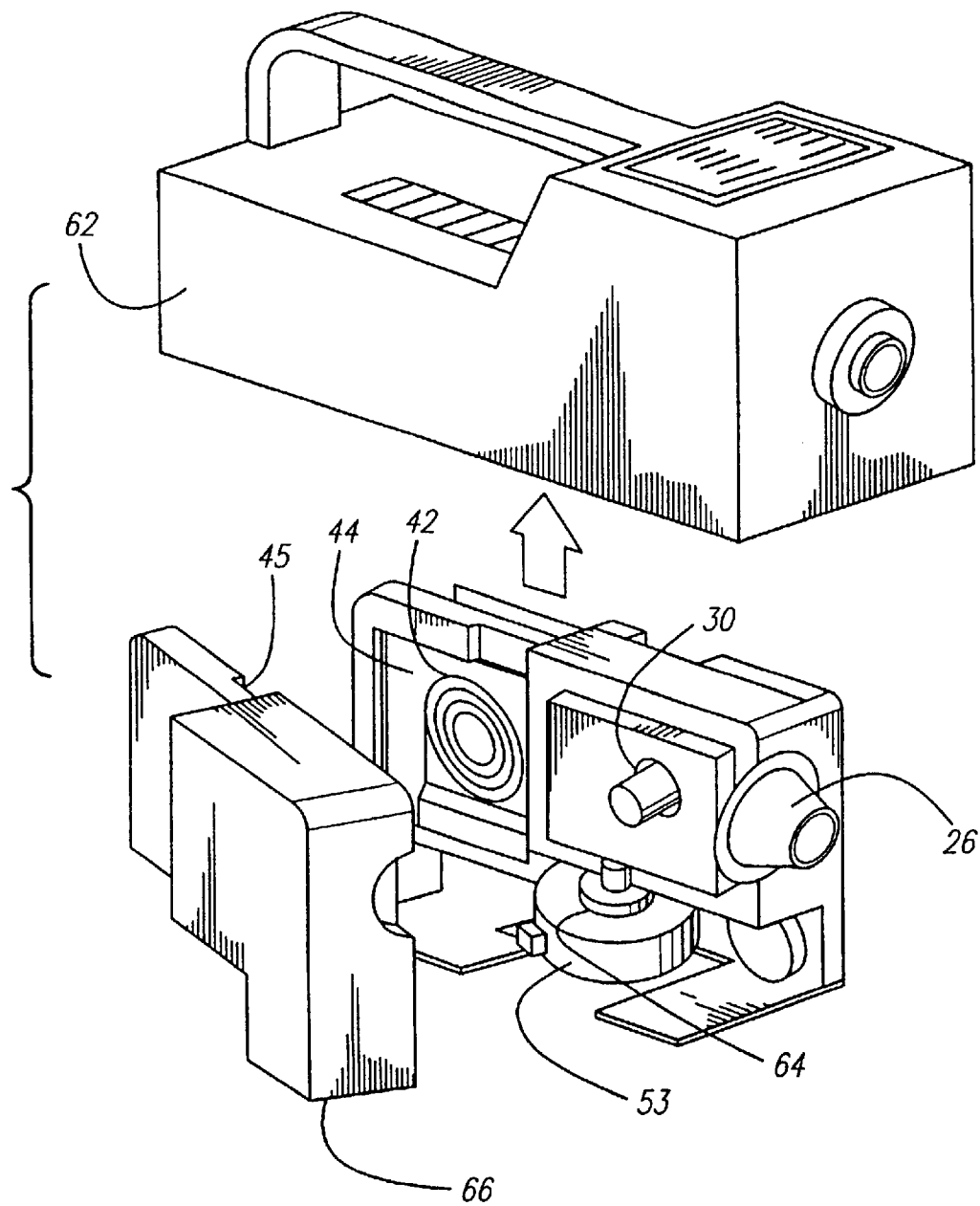
FIG. 2 shows an exploded view of a hand-held embodiment of an SAW/GC system according to the present invention.

FIG. 2 depicts an exploded view of a hand-held SAW/GC system according to the invention. Silicon preconcentrator collector 26, six-port GC valve 30, capillary column 42, SAW detector 53 of the SAW/GC system are illustrated in FIG. 2. Also illustrated are a housing 62 for containing the system, a sensor clamp 64 for securing SAW detector 53 in the system, and insulation section 66 for heat insulation.

In this embodiment, silicon preconcentrator collector 26 is integrated on the inlet of the system. To minimize power, the new system utilizes a digitally controlled, temperature ramped capillary column 42 which is able to provide a linear ramp to over 200° C. in 5 seconds. Capillary column 42 is made of metal and surrounded by an adhesive stiff plastic piece 44, such as Kapton made by 3M Company. Stiff plastic piece 44 secures capillary column 42 in the system. An air gap 45 is provided to allow air to flow in and out of the system. The system further minimizes power by utilizing a variable duty cycle pulse width modulation technique to apply current to metal capillary column 42 to heat it. The result is a system which can produce a chromatogram that will last only 10 seconds while utilizing minimum power.

A purpose of integrating a front end preconcentrator collector 26 into the SAW/GC system is to make it possible to test large samples at a rate of 5 to 10 liters of air per minute. The present invention utilizes many small nozzles or holes provided on a temperature controlled silicon collecting surface of preconcentrator collector 26 to adsorb and desorb vapors and particles from ambient air. Passivated silicon (silica) plates are used in preconcentrator collector 26. They are very effective for trapping "sticky" materials such as chemical vapors and are resistant to collecting dust and other interference that trouble "wipe" type collection systems that require physical contact with the object being tested.

Figure 3B:
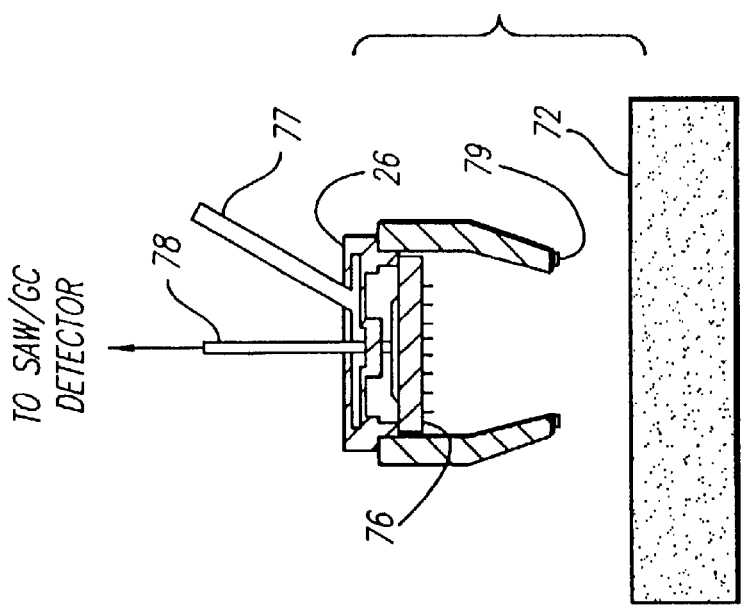
FIGS. 3A and 3B illustrate the operation of the preconcentrator collector in accordance with the present invention.
Figure 3A:
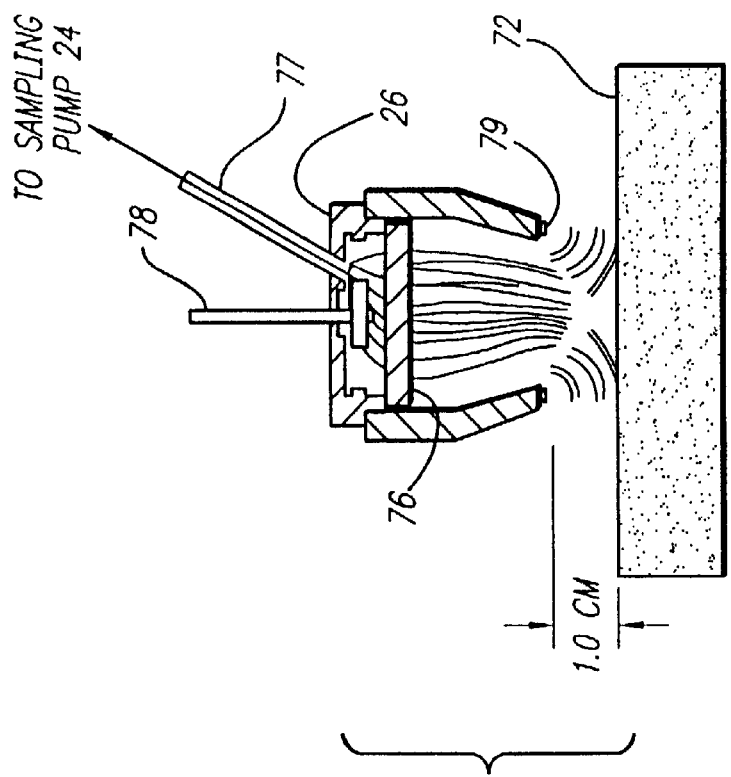
Figure 6:
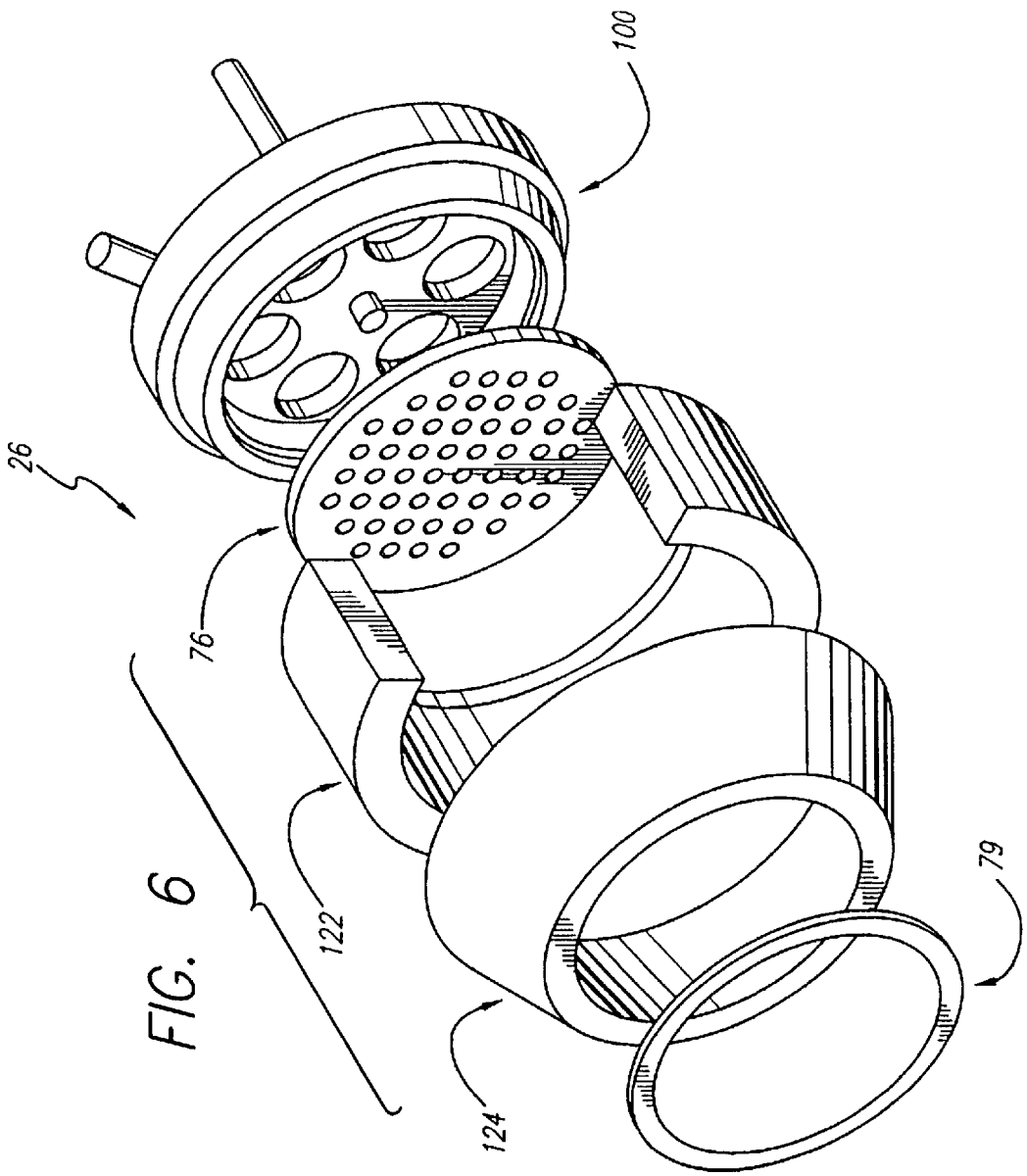
FIG. 6 shows an exploded view of the preconcentrator collector in accordance with the present invention.

FIGS. 3A and 3B illustrate the operation of preconcentrator collector 26 in accordance with the invention. Objects can be screened by the preconcentrator collector at distances up to several centimeters without actual physical contact between the preconcentrator collector and the objects. The preconcentrator collector operates in two steps. FIG. 3A illustrates high volume airflow during sampling. Air above the surface of an object 72 to be "smelled" is pulled through a stacked array of holes in micromachined silicon wafers 76 by a high capacity sampling pump through a sampling pipe 77. Aerosols entrained in the air stick to silicon wafers 76. Adsorption to the silica surface is enhanced by a low ambient air temperature and can be further enhanced by selective chemical coatings applied to the front surface of silicon wafers 76. After the adsorption, the temperature of silicon wafers 76 is quickly raised to desorb the trapped material. The desorbed vapor then enters the SAW/GC sensor through a transfer pipe 78, as illustrated in FIG. 3B. Attached to the inlet of preconcentrator collector 26 is an annular ring 79 with small directional holes. Pulsed air jets from the holes within the ring break up boundary layers air along the surface being sampled.

In this embodiment, the use of a puffing technique by employing a separate pulsed air supply can enhance the collection efficiency by several orders of magnitude over what would normally be expected from vapor pressure predictions.

Figure 7:
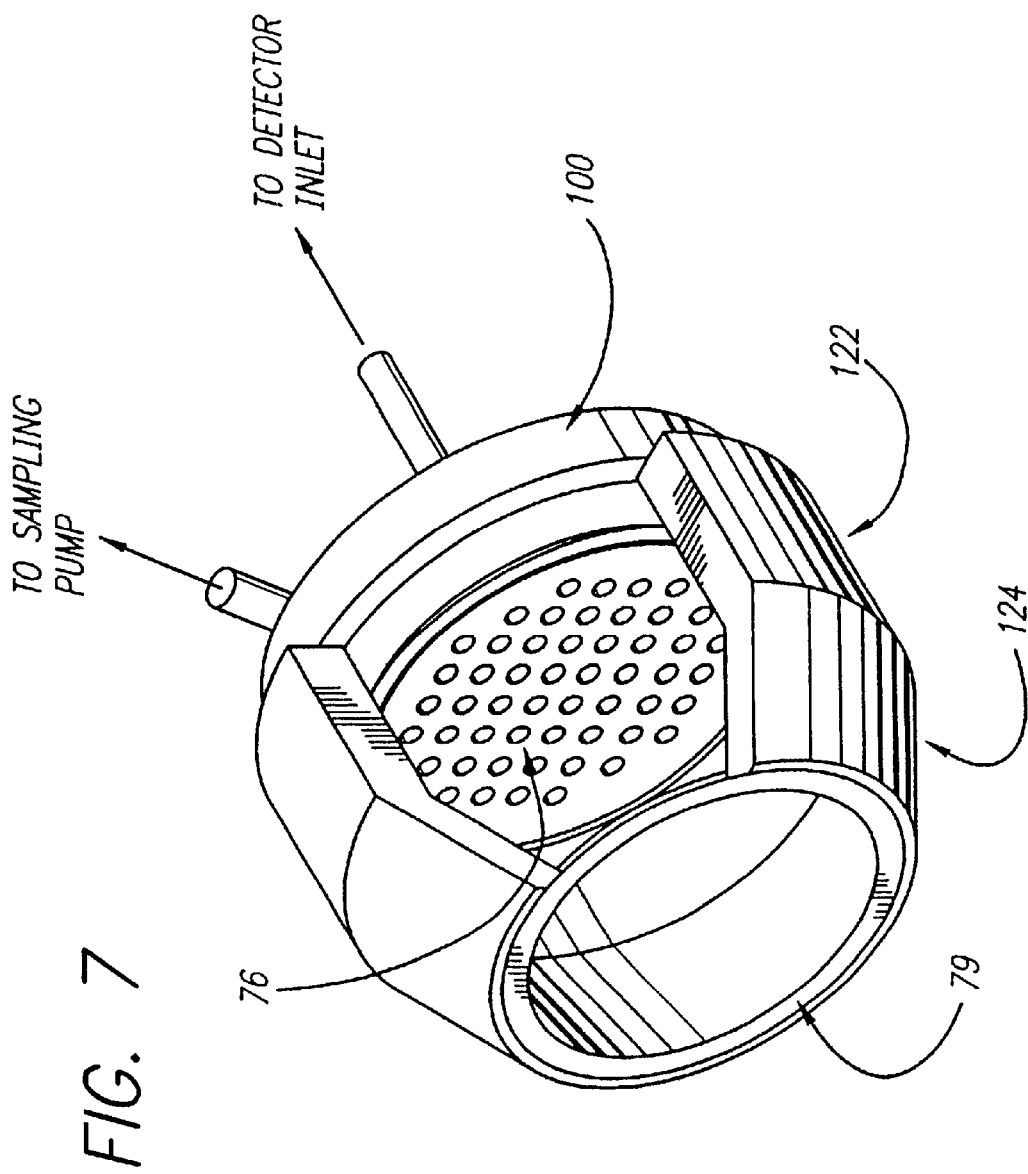
FIG. 7 shows the fully assembled preconcentrator collector shown in FIG. 6.

The preconcentrator collector comprises a stack of silicon or silica collector plates 76. The front and back sides of one such plate are shown in FIGS. 4A and 4B, respectively. As shown in FIGS. 4A and 4B, the collector includes a thin silicon or silica membrane 82 on which a plurality of through holes 84 are provided. A thin film resistive heater is attached to the front side of membrane 82. On its back side, a plurality of spacers 88 made of silicon dioxide, for example, are positioned between adjacent holes 84 across membrane 82 in one direction. A support ring 90 is provided around membrane 82. The collector plates allow air to pass through while trapping any aerosols within the air. After the aerosol material has been trapped on the surface of the collector plates, the temperature of the collector plates is raised rapidly by applying electric current to thin film heater 86 so as to desorb the trapped material as vapor. The vapor then enters the SAW/GC detector as illustrated in FIG. 3B. In effect, each hole 84 in a collector plate acts as a nozzle which directs impingement flow onto the surface of the plate beneath it.

Collector plates are used in pairs with offsetting through holes machined into them. Preliminary flow calculations for 0.01 to 0.1 cm diameter holes have been performed. For example, consider a wafer with 100 holes of 0.04 cm diameter. The calculations show that with only a two psi pressure drop across the wafer, a flow of 59.803 liters/minute can be achieved. This means that one liter of ambient air can be screened in one second.

Silicon is an ideal material for a number of reasons. First, it is relatively inert, particularly when oxidized, and can be easily cleaned. This is important since extraneous vapors are undesirable. Second, silicon can be accurately micromachined into structures with low thermal mass. The collector plates must be heated and cooled quickly with a minimum of applied power. For silicon wafers of 2.5 cm in diameter with 100 holes each having 0.025 cm in diameter, a surface area of 9.916 $cm^2$ will be available for collecting aerosols. The total mass for a wafer. of 0.0025 cm in thickness will be 0.0987 grams. This is 10 times less than the mass of a tubular type preconcentrator with equivalent surface area. Preliminary heating requirements as a function of wafer thickness have been calculated. The power required to raise the temperature of this wafer to 200° C. in 1 second is only 6.053 watts. Energy is small since power only needs to be applied only for 1 second and the thermal mass is low. Other materials may also be used instead of silicon to make the collector plates as long as they can be easily micromachined and easily cleaned. For example, fused quartz is one such material.

In FIG. 4A, the collecting surface on the front side of the collector plate may be made of epitaxial silicon on a low resistivity bulk silicon wafer. Anisotropic etching using ethylenediamine, pyrocatechol, and water (EDP) will create thick supports and a thin (5–10 $\mu$meter) membrane with holes. For a detailed description of this type of etching, refer to R. M. Finne and D. L. Klein, "Etching of Silicon Using EDP", J. Electrochem. Soc., Vol. 127, No. 12, December 1980; E. J. Staples, "High Resolution SWD Pattern Replication Without Photo Chemical Processing," Sonics and Ultrasonics Symposium Proceedings, November 1973, pp. 522–528; and R. D. Jolly and R. S. Muller, "Miniature Cantilever Beams Fabricated by Anisotropic Etching of Silicon," J. Electrochem. Soc., Vol. 127, No. 12, pp. 2751–2754, December 1980, all of which are hereby incorporated by reference. The final process step will involve vacuum deposition of a thin film resistive heater in the form of a meander line on the front surface. In one embodiment, wafers of one inch in diameter are used; in other embodiments, wafers of as large as six inches in diameter may be used. Based upon previous desorption experiments (See E. J. Staples, G. W. Watson, and W. J. Horton, "Temperature Programmed Desorption Characteristics of SAW Resonators", Proceedings of 1991 Ultrasonics Symposium, pp.317–320, Nov. 19, 1991, which is hereby incorporated by reference), and temperature and energy calculations, the temperature of the collector plates can be raised above 300° C. This will ensure rapid cleanup of the collecting surfaces of the collector plates.

Another important element of the preconcentrator collector design is the sampling valve. FIG. 5 shows an exploded view of a poppet-type sampling valve assembly 100 which may be used in the preconcentrator collector of the invention. As shown in FIG. 5, sampling valve assembly 100 comprises a sealing plate stopper 102 having six pumping ports 104, a sealing plate 106, and a base plate 108 which includes holes 110 and 112. Two pipes 77 and 78 are connected to the internal chamber of the preconcentrator collector through holes 110 and 112, respectively. Pipe 77 is a transfer pipe for transferring the concentrated gas desorbed from the collector plates to the SAW/GC detector. Pipe 78 is a sampling pipe for withdrawing ambient gas through the preconcentrator collector. Sampling pipe 78 is connected to a sampling pump. Transfer pipe 77 penetrates base plate 108 of sampling valve assembly 110 and sealing plate stopper 102. An opening 116 of transfer pipe 77 is disposed close to the collector plates without contacting them. On the other hand, sampling pipe 78 has an opening 117 connected to the internal chamber of the collector plates through hole 112 at base plate 108. Sealing plate 106 is disposed between base plate 108 and sealing plate stopper 102. When the ambient air is sucked through sampling pipe 78, sealing plate 106 moves close to base plate 108 and the ambient gas can flow through six ports 104 provided in sealing plate stopper 102. When the sampling pump connected to sampling pipe 78 is turned off and the desorbed gas is sucked toward the SAW/GC detector, sealing plate 106 moves toward sealing plate stopper 102, closing ports 104 on stopper 102. Then, the desorbed gas flows into transfer pipe 77 to the SAW/GC detector. This operation is also shown in FIG. 3B.

FIG. 6 shows an exploded view of a complete preconcentrator collector assembly 26 according to one embodiment of the invention. As shown in FIG. 6, preconcentrator collector assembly 26 comprises a poppet-type sampling valve 100, collector plates 76, body segment 122, a tip or nose cone 124, and an annular puffing ring 79. Body segment 122 and sampling valve 100 of preconcentrator collector assembly 26 will be heated by means of external electrical heaters (not shown). They are surrounded partially by insulation section 66 shown in FIG. 2 so that heat loss is minimized. Tip or nose cone 124 of preconcentrator collector assembly 26 may be fabricated from a machinable ceramic insulating material so that only a small amount of heat will pass through it to annular puffing ring 79 to heat the gas passing through ring 79. Since ceramic tip 124 and puffing ring 79 may come in contact with the object or person to be analyzed, it is important that both should not be too hot to touch. A temperature of approximately 60° C. is desirable. A completely assembled preconcentrator collector assembly 26 is shown in FIG. 7.

Figure 8A:
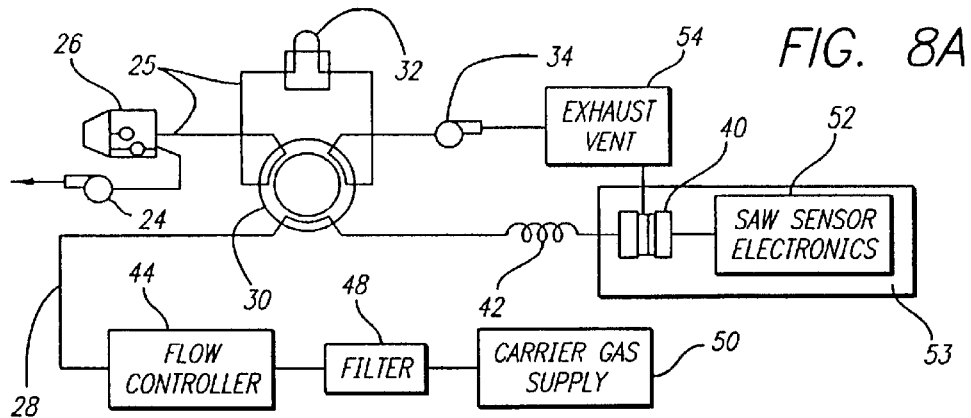
FIGS. 8A–8C show the operation of the SAW/GC system with the preconcentrator collector in accordance with the present invention.
Figure 8B:
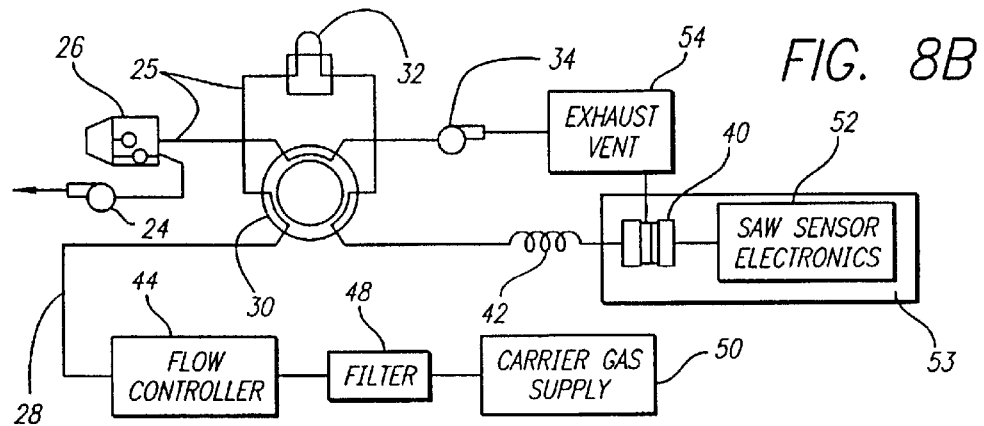
Figure 8C:
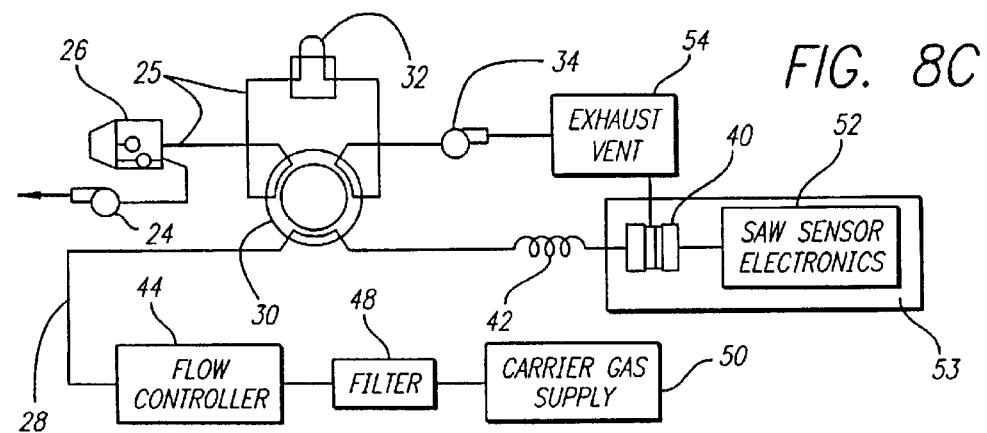

An example operation of the vapor detection and identification apparatus incorporating the inlet preconcentrator collector according to the present invention is illustrated in FIGS. 8A, 8B and 8C. When sampling pump 24 is turned on, the ambient gas begins to flow through preconcentrator collector 26. Chemical species to be sampled are adsorbed onto the surface of the collector plates in preconcentrator collector 26. Then, sampling pump 24 is switched off and the collector plates begin to be heated by applying electric current to thin film heater 86 to desorb any trapped materials to vapor. Chromatography valve 30 is set in the collection position as shown in FIG. 8A. A sample of collector 26 gas atmosphere and any condensable vapors contained therein is made to pass by means of a vacuum pump 34 through loop trap section 32 which is cooled by ambient air flow to a temperature sufficient to adsorb condensable vapor species. Loop trap section 32 is made of metal, such as brass, and condenses vapor species. The apparatus works with any ambient atmospheric gas, although air is the most Common gas to be searched for specific condensable vapor species.

During several seconds of sampling time, a carrier gas supply 50 causes helium gas to flow through a filter 48 and a flow controller 44, after which the helium gas is passed through chromatography valve 30, capillary separation column 42 and strikes the collection surface of the piezoelectric crystal sensor (not shown) in acoustic wave interferometer 40 in SAW detector 53. The preferred carrier gas is helium although the apparatus will operate with any inert carrier gas. During the initial sample collection cycle, the temperature of the acoustic interferometer sensor is raised by heat from a thermoelectric element (not shown) to a temperature of 120° C. sufficient to clean the sensor surface by causing all adsorbed vapors to desorb and pass out through an exhaust vent 54. After the sample collection time has expired, vacuum pump 34 is turned off, the temperature of acoustic wave interferometer 40 is reduced to a temperature of 5° C. sufficient to induce adsorption, and chromatography valve 30 is switched to the transfer position shown in FIG. 8B. After chromatography valve 30 has switched to the transfer position, the helium carrier gas flows through loop trap section 32, chromatography valve 30, capillary separation column 42, and through acoustic wave interferometer 40 to exhaust vent 54. At this time a short 0.0025 second pulse of electrical current is made to flow through loop trap section 32 which rapidly raises its temperature to 200° C. by means of resistive heating, and results in desorption of the trapped vapor species into the carrier gas. The carrier gas carries these desorbed vapors through the heated chromatography valve 32 to capillary separation column 42. Immediately following the heating of loop trap section 32 is a cooling-off period of from 1 to 10 seconds, during which the loop trap section 32 is cooled back to ambient temperature by conduction and radiation into the ambient air.

Following the transfer cycle, chromatography valve 30 is returned to the sample position. The preferred time for the transfer is about one second. After the transfer, a third cycle of the injection and analysis cycle is initiated, as illustrated in FIG. 8C. In this cycle, a new inlet sample vapor is condensed onto loop trap section 32, causing the adsorbed vapor species to be rapidly desorbed and injected into the carrier gas flowing through capillary separation column 42. The rapidly desorbed vapors are injected into capillary separation column 42 as an injection burst of vaporous material.

As is well known to practitioners of gas chromatography, individual vapor species passing through a separation column travel at different speeds and hence individual vapor species exit the separation column at different times. The preferred embodiment uses a 36 inch length of 0.008 inch inside diameter quartz capillary coated with 5% phenyl phase (DB-5) bonded to the backbone silicon atoms of a polysiloxane stationary phase polymer. The capillary separation column is commercially available from J & W Scientific, Folsom, Calif. The preferred embodiment maintains the capillary column at a temperature of 200° C. and all vapor species exit the column within a time span of 5 to 10 seconds.

The gas flow passes through the separation column to a nozzle which causes the individual vapor species to be focused onto a geometrically confined and focused area of the acoustic wave interferometer. The condensable vapor species are condensed at the interferometer due to the temperature gradient between the vapor stream and the collection surface at the interferometer. Uncondensed vapors pass on to the exhaust vent. The temperature gradient between the nozzle gas temperature and the piezoelectric crystal sensor of the interferometer is sufficiently large so that all of the condensable vapors are collected and focused into an area of maximum amplitude standing acoustic waves on the piezoelectric crystal sensor surface.

While the present invention has been described with respect to preferred embodiments and modifications thereto, it will be understood by those of ordinary skill in the art that further modifications may be made within the scope of the claims that follow. Accordingly, the scope of the invention is not to be in any way limited by the disclosure of the preferred embodiments, but to be determined by reference to the claims.

What is claimed is:

1. A preconcentrator collector for collecting and preconcentrating chemical vapors from a sample of ambient air, comprising:

a body having a sampling pipe and a tranfer pipe, said sampling pipe being connectable to a sampling pump for taking the sample of ambient air into the body; and a stack of disk-like collector plates each having a multiplicity of holes passing normally therethrough disposed in the body;

wherein after the sample is taken the collector plates trap the chemical vapors in the sample of ambient air and non-trapped vapors exit through an exhaust.

2. The preconcentrator collector of claim 1, further comprising a sampling valve disposed within said body.

3. The preconcentrator collector of claim 2, wherein the sampling valve is a poppet-type sampling valve comprising:

a sealing plate stopper having a plurality of pumping ports;

a sealing plate; and a base plate;

wherein the sealing plate is disposed between said sealing plate stopper and said base plate.

4. The preconcentrator collector of claim 3, further comprising a puffer attached to the body portion at the inlet and having a plurality of directional holes for taking the sample of ambient air.

5. The preconcentrator collector of claim 4, wherein the body portion includes a nosecone at the inlet and the puffer is attached to the nosecone.

6. The preconcentrator collector of claim 4, further comprising a sampling pipe and a transfer pipe, the sampling pipe having a first end coupled to the sealing plate stopper, the sealing plate and the base plate of the sampling valve and having a second end for connecting to a sampling pump, the transfer pipe having a first end coupled to the base plate of the sampling valve and a second end for connecting to a surface acoustic wave gas chromatographic (SAW/GC) detector, wherein in a sample collection cycle, the sample of ambient air is sucked into the preconcentrator collector by the sampling pump, with chemical vapors being trapped on the collector plates, and in an analysis cycle, the chemical vapors trapped by the collector plates are desorbed and transferred to the SAW/GC detector for detection and identification.

7. The preconcentrator collector of claim 2 further comprising a loop trap section disposed between ports of said sampling valve such that by way of appropriate switching of said sampling valve, said loop trap section is placed in fluid communication with said sampling pipe in a first instance or with said transfer pipe in a second instance, whereby said loop trap section may serve to adsorb chemical species, on the one hand, or to desorb said chemical species for purposes of analysis on the other hand.

8. A preconcentrator collector for collecting and preconcentrating chemical vapors from a sample of ambient air, comprising;
   a body having an inlet and an outlet, the outlet being connectable to a sampling pump for taking the sample of ambient air into the body;
   a stack of collector plates disposed in the body and made of a material selected from the group consisting of silicon, silica and fused quartz, each of the collector plates comprising:
      a membrane having a plurality of through holes spaced apart from one another,
      a film heater attached on a surface of the membrane for changing the temperature of the collector plate; and
   a sampling valve attached to the body;
   wherein after the sample is taken, the collector plates trap the chemical vapors in the ambient air and non-trapped vapors exit through an exhaust.

9. The preconcentrator collector of claim 8, wherein the sampling valve is a poppet type sampling valve comprising:
   sealing plate stopper having a plurality of pumping ports;
   a sealing plate; and
   a base plate;
   wherein the sealing plate is assembled between the sealing plate and the base plate.

10. An apparatus for identifying and analyzing chemical vapors from a sample of ambient air, comprising:
   a sampling pump;
   a preconcentrator collector for collecting and preconcentrating chemical vapors taken from the sample of ambient air, the preconcentrator collector comprising:
      a body having a sampling pipe and a tranfer pipe, the outlet being coupled to the sampling pump for taking the sample of ambient air into the body, and
      a stack of disk-like collector plates each having a multiplicity of holes passing normally therethrough disposed in the body, wherein after the sample is taken the collecting plates trap the chemical vapors in the ambient air and non-trapped vapors exit through an exhaust;
   means for desorbing said chemical vapors trapped on said collecting plates;
   separating means for separating individual vapor species in the chemical vapors desorbed from the collector plates of the preconcentrator collector according to their speeds in traveling through the separating means; and
   detecting means for detecting and identifying the individual vapor species output from the separation means.

11. The apparatus of claim 10, wherein the collector plates are made of a material selected from the group consisting of silicon, silica and fused quartz.

12. The apparatus of claim 10, wherein each of the collector plates comprises:
   a membrane having a plurality of through holes spaced apart from one another;
   a film heater attached on a surface of the membrane for changing the temperature of the collector plate.

13. The apparatus of claim 12, wherein the collector plates are made of a material selected from the group consisting of silicon, silica and fused quartz.

14. The apparatus of claim 12, wherein the separating means includes a metal column which is heatable by applying electric current thereto.

15. The apparatus of claim 10 further comprising a sampling valve attached to the body portion at the outlet.

16. The apparatus of claim 15 wherein the sampling valve is a poppet type sampling valve comprising:
   a sealing plate stopper having a plurality of pumping ports;
   a sealing plate; and
   a base plate;
   wherein the sealing plate is assembled between the sealing plate and the base plate.

17. The apparatus of claim 10 wherein the detecting means includes a surface acoustic wave gas chromatographic (SAW/GC) detector.

18. The apparatus of claim 10 further comprising:
   a gas chromatographic (GC) valve coupled between the preconcentrator collector and the separating means for coordinating transfer of chemical vapors from the preconcentrator collector to the detecting means via the separating means.

19. The apparatus of claim 18, further comprising a container coupled to the GC valve and containing a carrier gas which carries the chemical vapors from the preconcentrator collector to the SAW/GC detector via the separating means.

20. The apparatus of claim 19, wherein the carrier gas is helium.

* * * * *